(12) United States Patent
Defossez et al.

(10) Patent No.: US 11,672,581 B2
(45) Date of Patent: Jun. 13, 2023

(54) POWERED RETAINING SCREWDRIVER

(71) Applicant: DEPUY SYNTHES PRODUCTS, INC., Raynham, MA (US)

(72) Inventors: Henri Defossez, Neuchatel (CH); Rhett Rapier, Solothurn (CH); Simon Scherrer, Zurich (CH); Gregor Spreiter, Bern (CH); Mario Wyss, Egerkingen (CH); Reza Abedian, Solothurn (CH); Markus Büttler, Günsberg (CH); Simon Wampfler, Lohn-Ammannsegg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/887,572

(22) Filed: May 29, 2020

(65) Prior Publication Data
US 2021/0369318 A1 Dec. 2, 2021

(51) Int. Cl.
| A61B 17/88 | (2006.01) |
| A61B 17/86 | (2006.01) |
| A61B 17/00 | (2006.01) |
| A61B 17/56 | (2006.01) |

(52) U.S. Cl.
CPC ...... *A61B 17/8886* (2013.01); *A61B 17/8615* (2013.01); *A61B 17/8625* (2013.01); *A61B 2017/00477* (2013.01); *A61B 2017/564* (2013.01)

(58) Field of Classification Search
CPC combination set(s) only.
See application file for complete search history.

(56) References Cited

U.S. PATENT DOCUMENTS

| | | | |
|---|---|---|---|
| 2,329,398 | A | 9/1943 | Duffy |
| 2,604,912 | A | 7/1952 | Walker |
| 3,753,454 | A | 8/1973 | Totsu |
| 4,736,658 | A | 4/1988 | Jore |
| 5,139,499 | A | 8/1992 | Small et al. |
| 5,141,520 | A | 8/1992 | Boble et al. |
| 5,169,400 | A | 12/1992 | Muhling et al. |
| 6,033,405 | A | 3/2000 | Winslow et al. |
| 6,436,100 | B1 | 8/2002 | Berger |
| 7,325,470 | B2 | 2/2008 | Kay et al. |
| 9,387,025 | B2 | 7/2016 | Santangelo et al. |
| 9,451,999 | B2 | 9/2016 | Simpson et al. |
| 9,480,520 | B2 | 11/2016 | Rampersaud et al. |
| 9,526,553 | B2 | 12/2016 | Bess et al. |
| 9,681,895 | B2 | 6/2017 | Biedermann et al. |
| 2008/0269768 | A1 | 10/2008 | Schwager et al. |
| 2010/0249798 | A1 | 9/2010 | Sournac et al. |
| 2015/0250521 | A1 | 9/2015 | Poker et al. |

(Continued)

FOREIGN PATENT DOCUMENTS

| DE | 10042424 A1 | 3/2002 |
| FR | 2696925 A1 | 4/1994 |
| JP | 4271300 B2 | 6/2009 |

*Primary Examiner* — Sameh R Boles
(74) *Attorney, Agent, or Firm* — Fay Kaplun & Marcin, LLP (57) ABSTRACT

The invention relates to a system and method for driving orthopedic bone screws. In one aspect the driver includes a powered driving rod that is configured to releasably couple with a recess in a bone screw via a threaded system for coupling and uncoupling the screw from the driving rod.

8 Claims, 9 Drawing Sheets

(56) References Cited

U.S. PATENT DOCUMENTS

2016/0262819 A1 9/2016 May et al.
2016/0331553 A1 11/2016 Tanaka et al.
2018/0146990 A1 5/2018 Manzanares et al.
2018/0303522 A1* 10/2018 Wall ...................... A61B 34/20

* cited by examiner

POWERED RETAINING SCREWDRIVER

BACKGROUND

The treatment of many fractures requires the insertion of screws into the bone. For example, fractures of long bones may be treated by placing the bone into corrective alignment and inserting an intramedullary nail into a medullary canal of the aligned bone. The intramedullary nail may be fixed relative to the bone via fixation screws that are inserted into fixation holes that extend laterally through the intramedullary nail. The bone screws are driven into the bone using a screwdriver. In some cases, however, a bone screw may become inadvertently disengaged from the screwdriver during driving of the screw into the bone, which may result in loss of the bone screw and/or difficulty inserting the bone screw.

DETAILED DESCRIPTION

The present disclosure may be further understood with reference to the following description and the appended drawings, wherein like elements are referred to with the same reference numerals. The present embodiments relate to the treatment of a bone and, in particular, relate to the insertion of retaining bone screws. Retaining bone screws include retaining features configured to engage a screwdriver so that the bone screw is prevented from disengaging from the screwdriver during insertion of the bone screw, providing easier, faster and more secure insertion of bone screws. The exemplary embodiments describe a power-driven retaining screwdriver system for quick and easy insertion of retaining bone screws such as, for example, locking screws for an intramedullary nail system. It will be understood by those of skill in the art that the terms proximal and distal, as used herein refer to a direction toward (proximal) and away from (distal) a user of the system described herein. It will be further understood that, although the embodiments described herein are directed to an intramedullary nail system for long bones, the system of the present disclosure may also be utilized for other systems for use in driving any screw into any bone for any reason.

Figure 1:
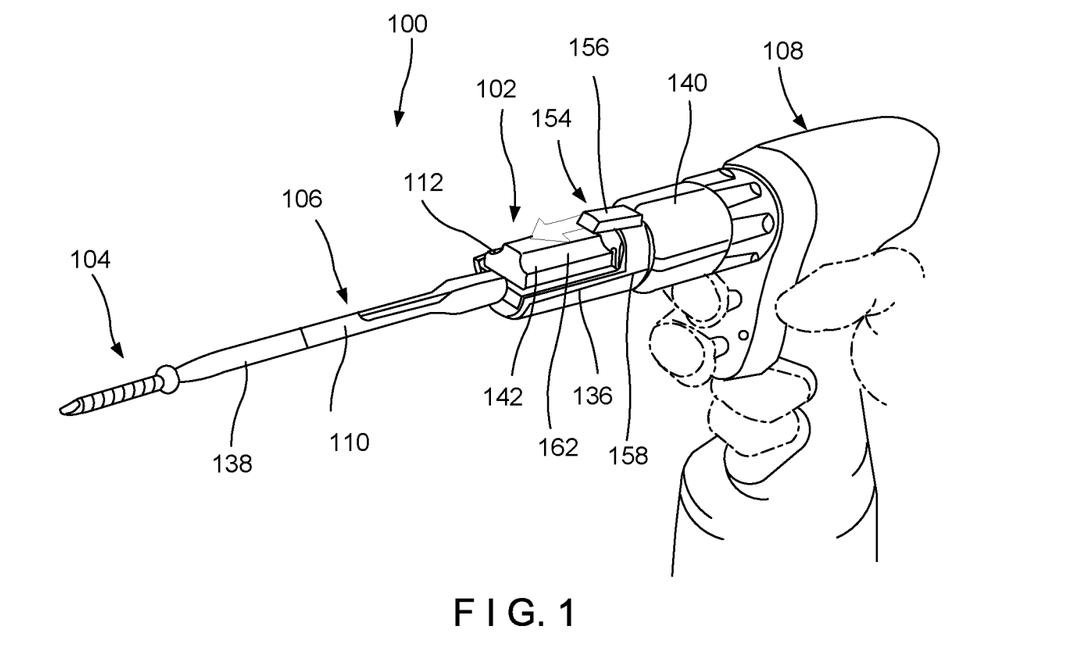
FIG. 1 shows a perspective view of a system according to an exemplary embodiment of the present disclosure.
Figure 2:
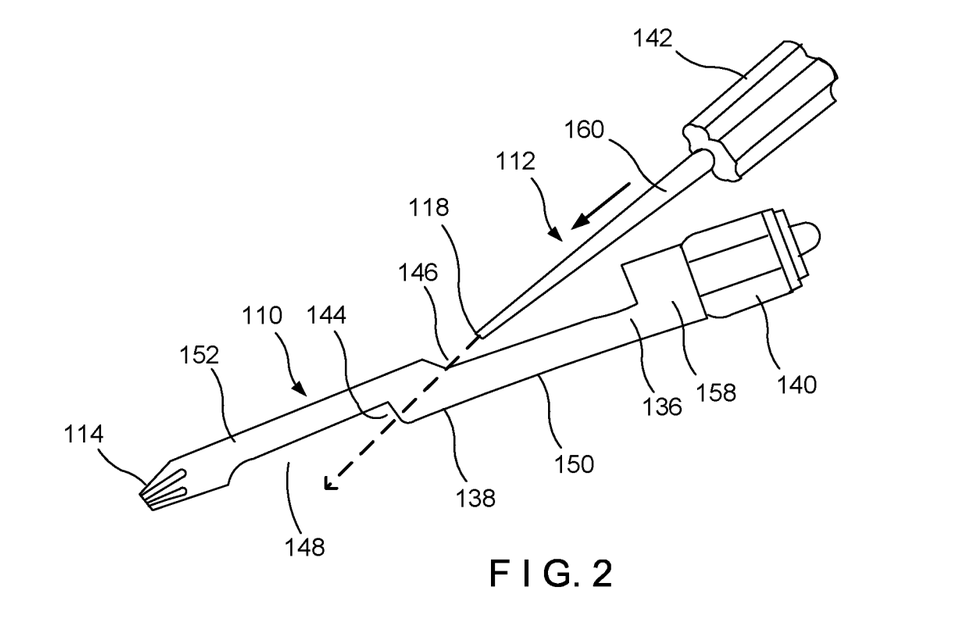
FIG. 2 shows a side view of the driver assembly, in a disassembled configuration, according to the system of FIG. 1.
Figure 3:
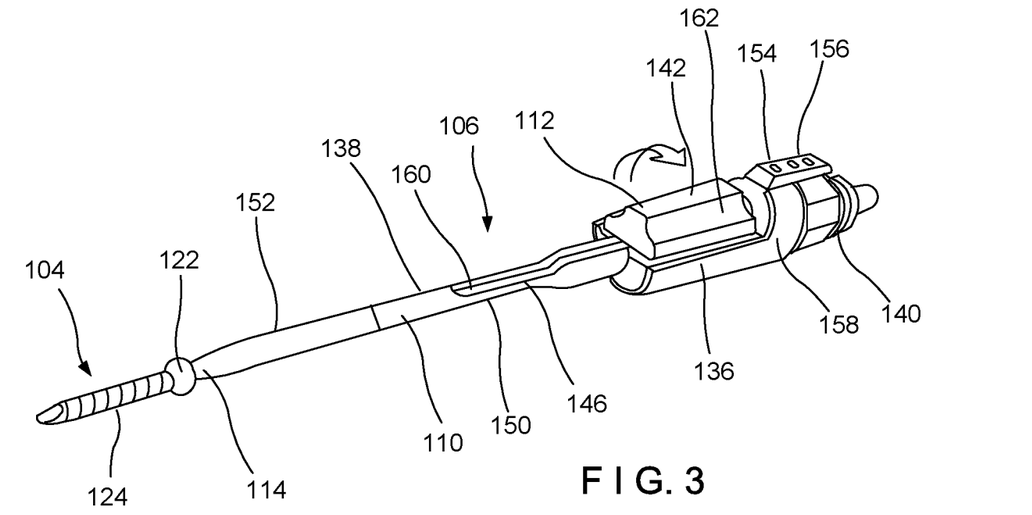
FIG. 3 shows a perspective view of a screwdriver assembly according to the system of FIG. 1 a cross-sectional view of the driver assembly engaging a bone screw according to the system of FIG. 1.
Figures 4, 5:
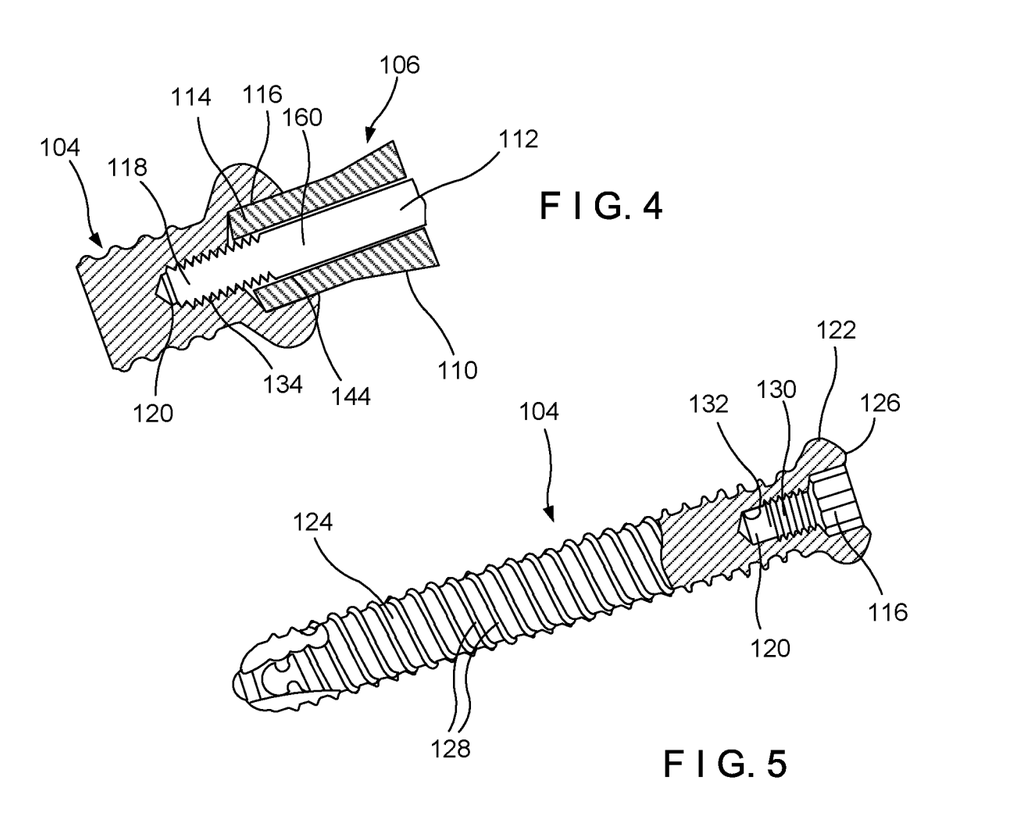
FIG. 4 shows a cross-sectional view of the driver assembly engaging a bone screw according to the system of FIG. 1
FIG. 5 shows a side view including a partial cross-section of the bone screw according to the system of FIG. 1.

As shown in FIGS. 1-5, a system 100 for treating a bone comprises a driving device 102 for driving a retaining screw 104 into a bone. As shown in FIG. 1, the driving device 102 includes a screwdriver assembly 106 configured to be coupled to a power driver 108. As shown in FIGS. 2-4, the screwdriver assembly 106 further includes a driving member 110 including a distal end 114 configured to engage a driving recess 116 of the screw 104 and a retaining member 112 including a distal end 118 configured to engage a retaining recess 120 of the screw 104.

As will be described in further detail below, the driving member 110 and the retaining member 112 are configured to be assembled such that the retaining member 112 is rotatable relative to the driving member 110 about a longitudinal axis thereof to engage the retaining recess 120 of the bone screw 104 while the driving member 110 engages the driving recess 116. Once the driving member 110 and the retaining member 112 have been assembled and engaged with the bone screw 104, the screwdriver assembly 106 is coupled to the power driver 108 to drive the bone screw 104 into a target portion of the bone.

In one embodiment, as shown in FIG. 5, the bone screw 104 includes a head portion 122 and a body portion 124 extending distally therefrom along a longitudinal axis. The body portion 124 includes threading 128 extending therealong for engaging the bone. A proximal end 126 of the head portion 122 includes the driving recess 116 extending distally thereinto, the driving recess 116 sized and shaped to receive and engage the distal end 114 of the driving member 110 therein so that, when the driving member 110 is rotated about a longitudinal axis thereof, a torsional force is applied to the bone screw 104 to drive the bone screw 104 into the bone. In one embodiment, the driving recess 116 includes a substantially circular central portion and a plurality of notches formed along a surface of the substantially circular central portion so that the notches extend radially outward from a longitudinal axis of the bone screw 104.

It will be understood by those of skill in the art that the driving recess 116 may include any number of notches in any of a variety of configurations so long as the notches are sized and shaped to engage corresponding portions of the distal end 114 of the driving member 110. It will also be understood by those of skill in the art, that the driving recess 116 may have any of a variety of configurations so long as the driving recess 116 is non-rotatably engageable with the driving member 110. For example, in another embodiment, the driving recess 116 may have a hexagonal cross-section. In another example, the driving recess 116 may be star shaped. It will be understood by those of skill in the art, however, that the driving recess 116 may have any of a variety of shapes so long as a torsional applied to the driving member 110 is transferred via the driving recess 116 to the bone screw 104.

The proximal end 126 of the head portion 122 also includes the retaining recess 120 which extends distally from the driving recess 116. The retaining recess 120 has a cross-sectional area smaller than that of the driving recess 116 and is configured to receive and engage the distal end 118 of the retaining member 112 therein. In one embodiment, the retaining recess 120 includes threading 130 along an interior surface 132 configured to engage a corresponding threading 134 extending along the distal end 118 of the retaining member 112. Engagement between the retaining recess 120 and the distal end 118 of the retaining member 112 aids in retaining (e.g., holding) the bone screw 104 coupled to the screwdriver assembly 106 while the bone screw 104 is being driven into the bone.

As described above, the screwdriver assembly 106 includes the driving member 110 and the retaining member 112. The driving member 110 includes a housing 136, a shaft 138 extending distally from the housing 136 to the distal end 114, and a coupling element 140 extending proximally from the housing 136. The coupling element 140 is configured to be coupled to a corresponding portion of the power driver 108 so that, when coupled, powering of the power driver 108 will rotate the driving member 110 about a longitudinal axis thereof to drive the bone screw 104 into the bone.

The housing 136 and the shaft portion 138 include a channel 144 extending longitudinally therethrough for receiving the retaining member 112 therein. As will be described in further detail below, a portion of the channel 144 extending through the housing 136 is sized and shaped to receive a control knob 142 of the retaining member 112 while a portion of the channel 144 extending through the shaft portion 138 is sized and shaped to receive a rod portion 160 of the retaining member 112 therein. A first longitudinal slot 146 extends longitudinally along a first side of the housing 136 and a proximal portion 150 of the shaft 138 so that the channel 144 is open to an exterior of the driving member 110 along the first side via the first longitudinal slot 146.

In one embodiment, the first longitudinal slot 146 does not extend through a proximal end 158 of the housing 136. A second longitudinal slot 148 extends longitudinally along a distal portion 152 of the shaft 138 along a second side of the driving member 110 opposite the first side so that the channel 144 is open to an exterior of the driving member 110 along the second side via the second longitudinal slot 148. The second longitudinal slot 148, however, does not extend to the distal end 114 so as not to interfere with an engagement between the driving member 110 and the driving recess 116 of the bone screw 104 and to hold a distal portion of the retaining member 112 therein once the retaining member 112 has been assembled therewith, as will be described in further detail below.

As described above, the distal end 114 is sized and shaped to correspond to the size and shape of the driving recess 116 so that, when the distal end 114 is engaged with the driving recess 116 of the bone screw 104, rotation of the driving member 110 correspondingly rotates the bone screw 104 to drive the bone screw 104 into (or out of) the bone. In one example, the distal end 114 of the shaft 138 of the driving member 110 includes a plurality of radially extending protrusions sized and shaped to be received within corresponding notches of the driving recess 116. In another example, the distal end 114 may have a hexagonal or star shaped cross-section. It will be understood by those of skill in the art, however, that the distal end 114 may have any of a variety of sizes, shapes and configurations so long as the distal end 114 is configured to non-rotatably engage the driving recess 116 of the bone screw 104 so that rotation of the driving member 110 rotatably drives the bone screw 110 into the bone.

The driving member 110 also includes a locking mechanism 154 for locking the retaining member 112 relative to the driving member 110. The locking mechanism 154 is movable between an unlocked configuration (FIG. 3) and a locked configuration (FIG. 1). In the unlocked configuration, when the retaining member 112 is assembled with the driving member 110, the retaining member 112 is permitted to be rotated about the longitudinal axis thereof relative to the driving member 110. In the locked configuration, the retaining member 112 is locked with respect to the driving member 110 so that the retaining member 112 is not rotatable relative thereto.

In one embodiment, the locking mechanism 154 includes a sliding lock 156. The sliding lock 156 may be positioned at the proximal end 158 of the housing 136 so that, in the unlocked configuration, the sliding lock 156 is withdrawn proximally so that it does not extend over any portion of the first longitudinal slot 146 and/or the channel 144. When moved distally into the locked configuration, however, the sliding lock 156 extends distally over a proximal end of the first longitudinal slot 146 so that, when a retaining member is received within the channel 144 of the driving member 110, the sliding lock 156 extends over and engages a portion of the control knob 142 received within the housing 136. Thus, when in the locked configuration, the sliding lock 156 fixes the control knob 142 of the retaining member 112 within the housing 136 of the driving member 110 and prevents a rotation of the retaining member 112 relative to the driving member 110. In this embodiment, in the locked configuration, a flat surface of the sliding lock 156 overlies and engages a corresponding flat surface of the control knob 142 preventing the knob 142 and the retaining member 112 from rotating relative to the driving member 110.

The retaining member 112 includes the control knob 142 and the rod 160 extending distally therefrom to the distal end 118. The control knob 142 is sized and shaped to be received within the housing 136 and is configured to be inserted into the housing 136 via the first longitudinal slot 146. A length of the control knob 142 is smaller than a length of the housing 136 so that, as will be described in further detail below, the retaining member 112 is longitudinally movable relative to the driving member 110. In one embodiment, a difference in length between the control knob 142 and the housing 136 corresponds to a length of the retaining recess 120 of the bone screw 104. In one embodiment, the control knob 142 also includes grooves 162 or other gripping features facilitating manual rotation of the control knob 142 relative to the driving member 110 by a user (e.g., surgeon).

As described above, the rod 160 extends distally from the control knob 142 to the distal end 118. In one embodiment, the rod 160 is rigid and the distal end 118 of the retaining member 112 includes the threading 134 extending thereal-ong configured to engage the threading 130 of the retaining recess 120. Thus, when the driving member 110 and the retaining member 112 are assembled and the distal end 118 of the driving member 110 is engaged with the driving recess 116 of the bone screw 104, rotation of the retaining member 112 relative to the driving member 112 via, for example, the control knob 142, in a first direction about a longitudinal axis thereof, engages the threading 134 with the retaining recess 120 to couple the retaining member 112 to the bone screw 104. It will be understood by those of skill in the art that once the distal end 118 has been engaged with the retaining recess 120, rotating the retaining member 112 relative to the driving member 110 in a second direction opposite the first direction unthreads the distal end 118 from the retaining recess 120, permitting the retaining member 112 to be disengaged from the retaining recess 120.

In one embodiment, the driving member 110 and the retaining member 112 are assembled to form the driver assembly 106 by distally inserting the rod 160 through the first longitudinal slot 146 at an angle relative to the driving member 110, as shown in FIG. 2, so that the distal end 118 protrudes out of the second longitudinal slot 148. As the retaining member 112 is moved further distally relative to the driving member 110, the retaining member 112 is also moved toward the driving member 110, decreasing an angle therebetween until the retaining member 112 extends substantially coaxially with the driving member 110 as the control knob 142 is received within the housing 136 of the driving member 110. At the same time, retaining member 112 is slid distally within the channel 144 to move the distal end 118 of the retaining member 112 until it extends distally past the distal end 114 of the driving member 110.

As shown in FIG. 3, once the driver assembly 106 is assembled, the distal end 114 of the driving member 110 is inserted into the driving recess 116 of the bone screw 104 to engage the driving recess 116. The retaining member 112 is then rotated relative to the driving member 110, in a first direction about the longitudinal axis of the retaining member 112 as a user manually rotates the control knob 142. Upon engagement of the driver assembly 106 with the bone screw 104 to be driven into the bone, the sliding lock 156 is moved from the unlocked configuration to the locked configuration by, in this embodiment, sliding the sliding lock 156 distally until it overlies a portion of the control knob 142 engaging a surface of the control knob 142 to hold the control knob 142 within the housing 136 and prevent further rotation of the retaining member 112 relative to the driving member 110. The driver assembly 106 is then coupled to the power driver 108 to form the driving device 102.

In one embodiment, the coupling element 140 is inserted into and engaged with, for example, a chuck of the power driver 108. It will be understood by those of skill in the art, however, that the driver assembly 106 may be coupled to the power driver 108 in any of a number of ways so long as the driver assembly 106 is coupled to the power driver 108 in a manner that facilitates a powered rotation of the driving assembly.

It will also be understood by those of skill in the art that although the exemplary embodiment describes the driver assembly as engaged with the bone screw 104 prior to coupling the driver assembly 106 to the power driver 108, in another embodiment, the driver assembly 106 may be coupled to the power driver 108 prior to engaging the bone screw 104. In particular, the driver assembly 106 may be coupled to the power driver 108 in the unlocked configuration so that, when the distal end 114 of the driving member 110 is engaged with the driving recess 116 the retaining member 112 may be rotated relative to the driving member 110, in the first direction, so that the distal end 118 of the retaining member 112 threadedly engages the retaining recess 120. Once the driver assembly 106 has been engaged with the bone screw 104, the sliding lock 156 is moved toward the locked configuration.

Once the driver assembly 106 has been engaged with the bone screw 104, the driving device 102 may be used to power-drive the bone screw 104 into a target portion of a bone as would be understood by those skilled in the art. In particular, the power driver 108 rotates the driver assembly 106 to drive the bone screw 104 into the bone. It will be understood by those of skill in the art that since the driving member 110 and the retaining member 112 are locked with respect to one another, both the driving member 110 and the retaining member 112 are rotated so that the bone screw 104 remains retained on the driver assembly 106 as it is being driven into the bone.

Once the bone screw 104 has been driven into the bone, as desired, the sliding lock 156 is moved toward the unlocked configuration and the retaining member 112 is then rotated in the second direction relative to the driving member 110 to disengage retaining member 112 from the retaining recess 120 at which point the screw 104 may be disengaged from the device 102. When the screw 104 has been completely disengaged (e.g., unthreaded) from the driving member 110, the driving device 102 is withdrawn proximally from the body, leaving the bone screw 104 implanted in the target portion of the bone at which point a new screw 104 may be coupled to the device 102 and the process may be repeated as desired.

Figure 6:
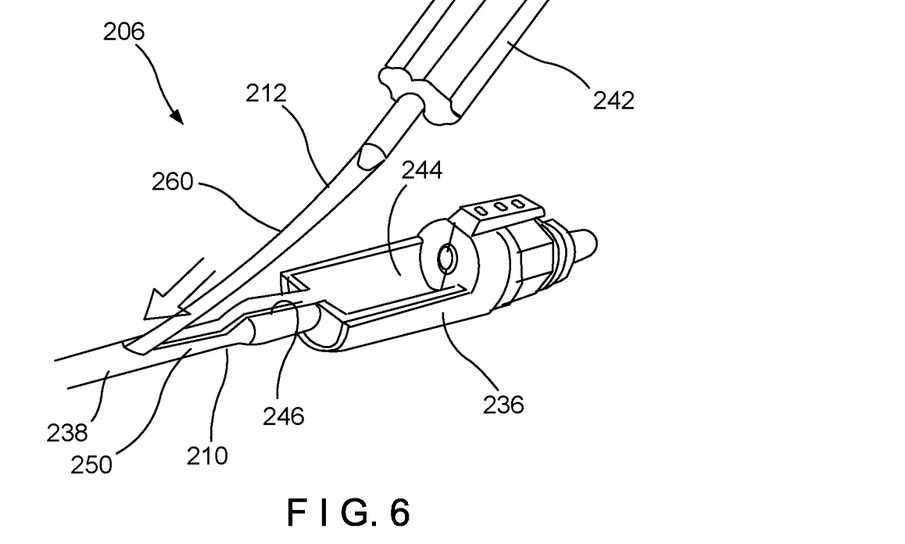
FIG. 6 shows a perspective view of a driver assembly according to another exemplary embodiment of the present disclosure.

As shown in FIG. 6, a driver assembly 206 according to another exemplary embodiment may be substantially similar to the driver assembly 106, as described above with respect to the system 100. The driver assembly 206 is couplable to a power driver substantially similar to the power driver 108 to drive a retaining bone screw substantially similar to the bone screw 104 into a bone. Similarly to the driver assembly 106, the driver assembly 206 includes a driving member 210 assembled with a retaining member 212. The driving member 210 and the retaining member 212 are substantially similar to the driving member 110 and the retaining member 112, respectively, except that a rod 260 of the retaining member 212 is somewhat flexible so that a shaft 238 of the driving member 210 does not require a second longitudinal slot to facilitate insertion of the retaining member 212 into a channel 244 of the driving member 212. Rather, as will be described in further detail below, the rod 260 is flexed relative to a longitudinal axis thereof as it is inserted distally through the channel 244 via a longitudinal slot 246 along a proximal portion 250 of a shaft 238 of the driving member 210.

Similarly to the driving member 110, the driving member 210 includes a housing member 236 along with the shaft 238 extending distally therefrom to a distal end configured to engage a driving recess of the bone screw and a coupling element 240 extending proximally therefrom for engaging a corresponding portion of the power driver. The longitudinal channel 244 extends through both the shaft 238 and the housing 236. In particular, a portion of the channel 244 extending along the housing 236 is sized and shaped to receive a control knob 242 of the retaining member 212 while a portion of the channel 244 extending through the shaft 238 is sized and shaped to receive the rod 260 of the retaining member 212. The longitudinal slot 246 extends through the proximal portion 250 of the shaft 238 and the housing 236 so that the channel 244 is open to an exterior of the driving member 210 via the longitudinal slot 246.

As described above, the retaining member 212 is substantially similar to the retaining member 112, including the control knob 242 and the rod 260 extending distally therefrom to a distal end configured to engage a retaining recess of the bone screw, substantially similarly to the distal end 118 of the retaining rod 112. The rod 260 in this embodiment, however, is flexible so that the rod 260 is longitudinally flexed as the distal end thereof is inserted through the longitudinal slot 246 and moved distally through the channel 244. The retaining member 212 is moved distally relative to the driving member 210 until the control knob 242 is received within the housing 236 and the distal end of the retaining member 212 extends distally past the distal end of the driving member 210. Once the retaining member 212 has been assembled with the driving member 210, as described, to form the driver assembly 206, the driving member 210 and the retaining member 212 are substantially coaxial relative to one another.

It will be understood by those of skill in the art that although the rod 260 is described as axially flexible, the rod 260 is sufficiently torsionally rigid so that, as the retaining member 212 is rotated relative to the driving member 210, its distal end threadedly engages and disengages to/from the retaining recess of the bone screw in the same manner described above for the retaining member 112 and the screw 104. Once the driver assembly 206 has been assembled, as described above, the driver assembly 206 may be engaged with the bone screw and coupled to the power driver in a manner substantially similar to the system 100. The bone screw may then be power-driven into the bone. Once the bone screw has been completely inserted into the bone, the retaining member 212 is disengaged from the retaining recess of the bone screw so that the driver assembly 206 may be withdrawn from the body.

Figure 7:
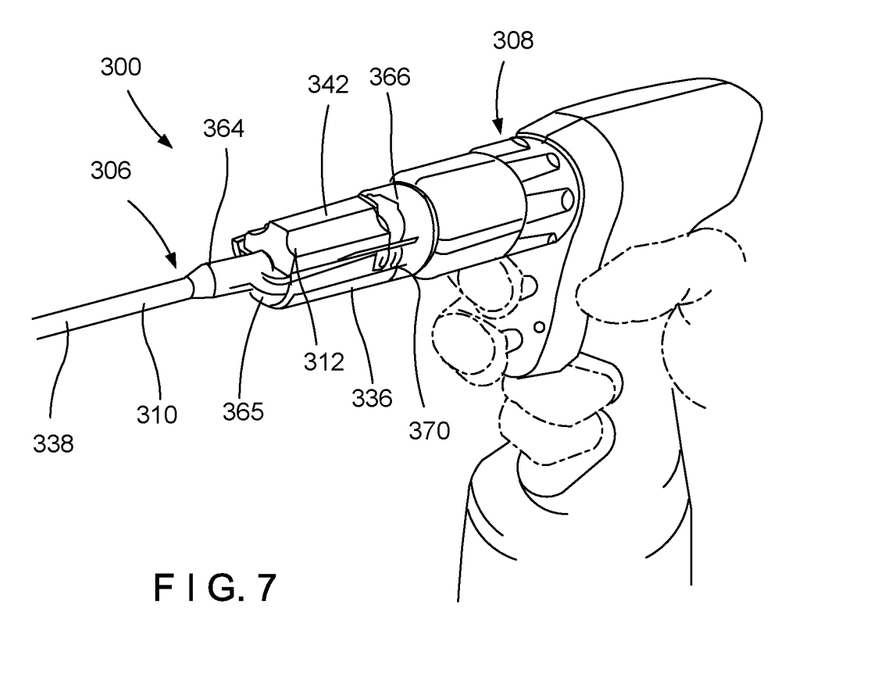
FIG. 7 shows a perspective view of a system according to another exemplary embodiment of the present disclosure.
Figure 8:
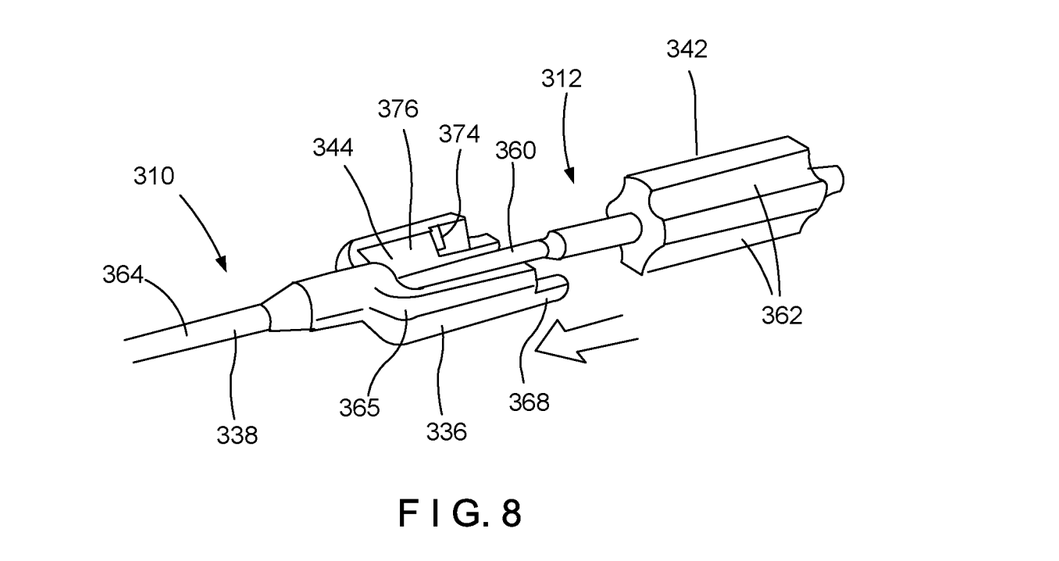
FIG. 8 shows a perspective view of a driver assembly according to the system of FIG. 7.
Figure 9:
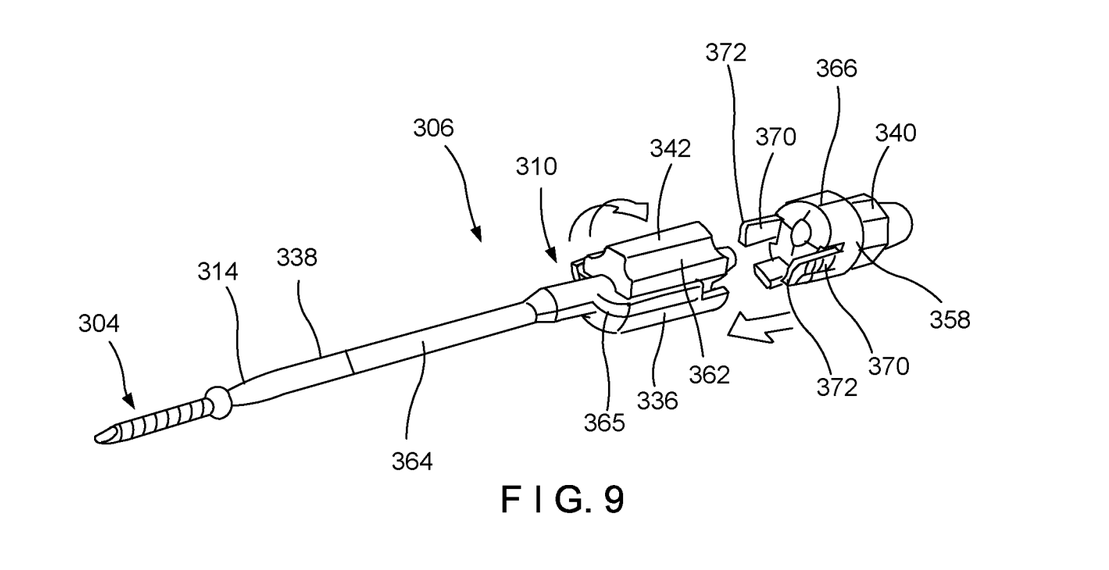
FIG. 9 shows another perspective view of the driver assembly according to the system of FIG. 7.

As shown in FIGS. 7-9, a system 300 according to another exemplary embodiment is substantially similar to the system 100, comprising a driver assembly 306 couplable to a power driver 308 to drive a retaining bone screw 304 into a bone. The power driver 308 and the bone screw 304 are substantially similar to the power driver 108 and the bone screw 104, as described above with respect to the system 100. The driver assembly 306 is also substantially similar to the driving assemblies 106, 206 described above, including a driving member 310 and a retaining member 312 for retaining the bone screw 304 while driving the bone screw 304 into the bone. The retaining member 312 may be substantially similar to the retaining member 112 described above, including a control knob 342 and a rod 360 extending distally therefrom to a distal end configured to engage a retaining recess of the bone screw 304. In this embodiment, however, the driving member 310 is comprised of two portions—a first portion 364 and a second portion 366 couplable to one another to form the driving member 310.

The first portion 364 includes a distal portion 365 of a housing 336 and a shaft 338 extending distally therefrom to a distal end 314 configured to engage a driving recess of the bone screw 304. A channel 344 extends longitudinally through the first portion 364—through the shaft 338 and the distal portion 365 of the housing 336—to receive the retaining member 312 therein. Similarly to the driving members 110, 210, a portion of the channel 344 extending through the shaft 338 is sized and shaped to receive the rod 360 of the retaining member 312 therein while a portion of the channel 344 extending through the housing 336 is sized and shaped to receive the control knob 342 of the retaining member 312 therein.

The channel 344 is open to an exterior of the first portion 364 at a proximal end 368 thereof so that the retaining member 312 is distally insertable into the channel 344 along a longitudinal axis thereof via the proximal end 368 of the first portion 364. While the shaft 338 does not include any longitudinal slots along any portion thereof, the portion of the channel 344 extending through the housing 336 is open to an exterior thereof along a longitudinal side thereof so that the control knob 342, when received therein, is accessible to a user so that the user may rotate the retaining member 312 relative to the driving member 310 via the control knob 342.

The second portion 366 is configured to be coupled to the proximal end 368 of the first portion 364 to hold the retaining member 312 within the first portion 364, in an operative configuration. The second portion 366 is couplable to the proximal end 368 so that, when the retaining member 312 has been completely inserted through the channel 344 of the first portion 364, the second portion 366 is coupled to the first portion 364, proximally of the control knob 342 of the retaining member 312 to hold the retaining member 312 therein. The second portion 366 includes a proximal portion 358 of the housing 336 and a coupling element 340 extending proximally therefrom for engaging a corresponding portion of the power driver 308. The second portion 366 also includes a plurality of snap arms 370 extending distally from the proximal portion 358 of the second portion 366 to engage the proximal end 368 of the first portion 364.

In one embodiment, the snap arms 370 include locking tabs 372 extending radially outward from distal ends thereof, the locking tabs 372 configured to engage corresponding grooves 374 along an interior surface 376 of a portion of the channel 344 extending along the proximal end 368 of the first portion 364. The snap arms 370 are biased toward an initial configuration so that, as the second portion 366 is moved toward the first portion 364, the snap arms interface with the proximal end 368 of the first portion 364 to deflect radially inward until the locking tabs 372 are received within the grooves 374. Once the locking tabs 372 are received within the grooves 374, the snap arms 370 revert toward their biased configuration, to lock the second portion 366 relative to the first portion 364. When it is desired to decouple the second portion 366 from the first portion 364, the snap arms 370 may be pressed radially inward to disengage the locking tabs 372 from the grooves 374.

The snap arms 370 are positioned so that, when the second portion 366 is moved into engagement with the first portion 364, the snap arms 370 are received within longitudinally extending grooves 362 along the control knob 342 of the retaining member 312 so that, when the second portion 366 is coupled with the first portion 364, the retaining member 312 is prevented from rotated relative to the driving member 310. Thus, upon assembly of the retaining member 312 with the first portion 364, the first portion 364 of the driving member 310 and the retaining member 312 should be engaged with the bone screw 304 prior to the coupling of the second portion 366 with the first portion 364.

It will be understood by those of skill in the art that the driving member 310 and the retaining member 312 may be engaged with the bone screw 304 in a manner substantially similar to the system 100. In particular, once the first portion 364 and the retaining member 312 have been assembled, the distal end 314 of the driving member 310 may be inserted into and engaged with a driving recess of the bone screw 304. The retaining member 312 may then be rotated relative to the first portion 364 about a longitudinal axis thereof via, for example, the control knob 342, so that the distal end of the retaining member 312 engages the retaining recess of the bone screw 304. Once the bone screw 304 has been engaged, the second portion 366 is coupled to the first portion 364, fixing the retaining member 312 within the channel 344 and locking the retaining member 312 relative to the driving member 310.

It will be understood by those of skill in the art that the driver assembly 306, as described above may be coupled to the power driver 308 and used to drive the bone screw 304 into the bone in a manner substantially similar to the system 100.

Figure 10:
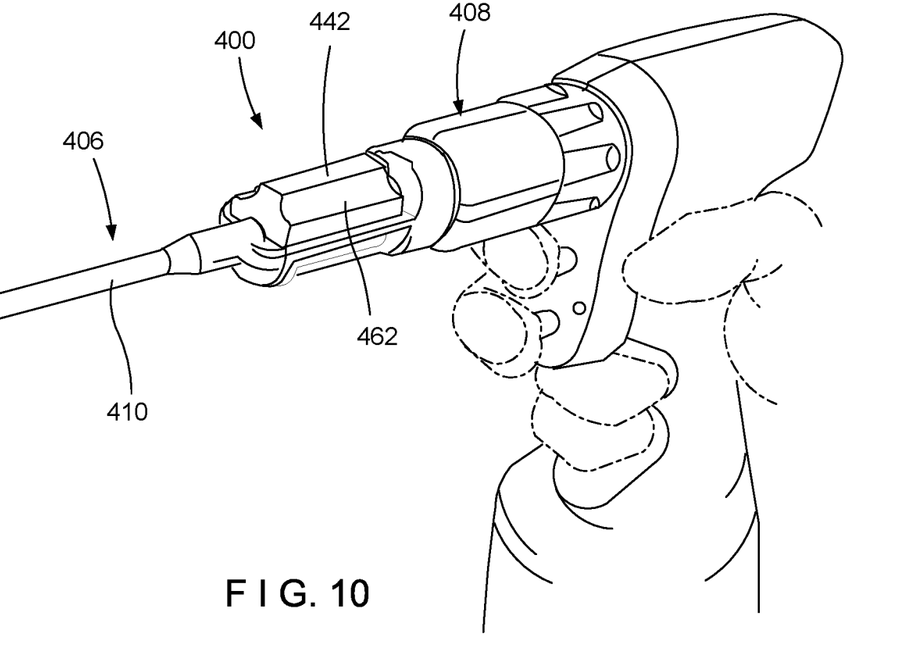
FIG. 10 shows a perspective view of a system according to yet another exemplary embodiment of the present disclosure.
Figure 11:
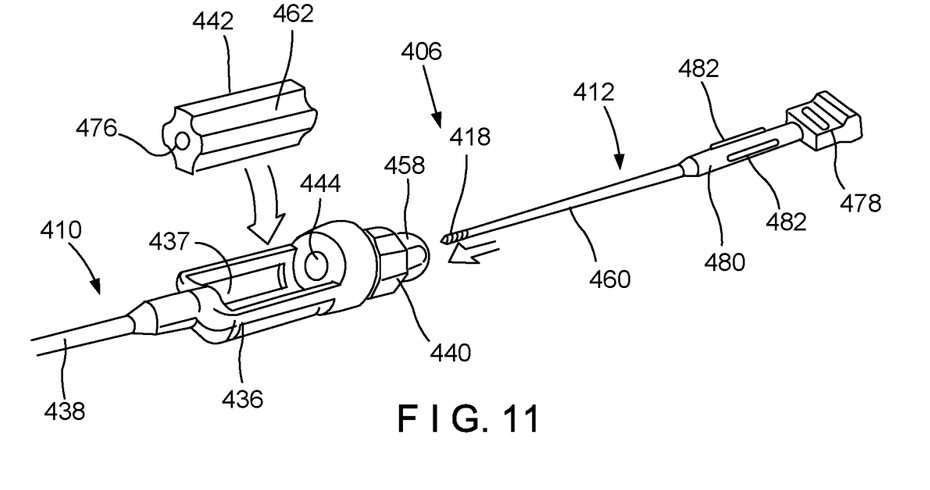
FIG. 11 shows a perspective view of a driver assembly according to the system of FIG. 10, in an unassembled configuration.
Figure 12:
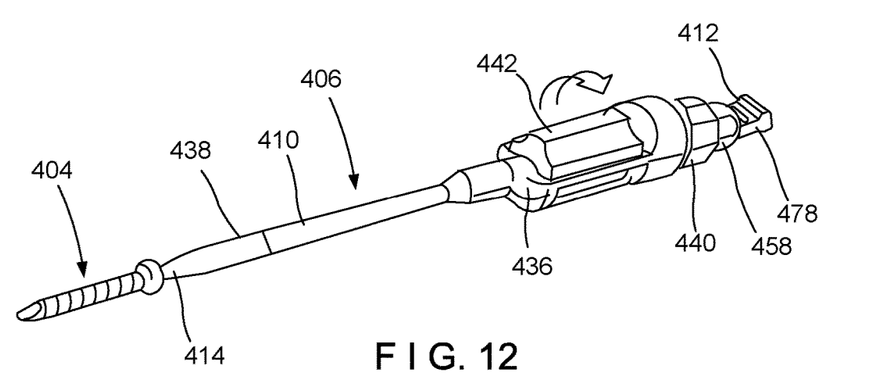
FIG. 12 shows a perspective view of the driver assembly according to the system of FIG. 10, in an assembled configuration.

As shown in FIGS. 10-12, a system 400 according to another exemplary embodiment may be substantially similar to the systems described above, comprising a driver assembly 406 couplable to a power driver 408 to drive a retaining bone screw 404 into a bone. The power driver 408 and the bone screw 404 are substantially similar to the power driver 108 and the bone screw 104, respectively, described above with respect to the system 100. Similarly to the systems above, the driver assembly 406 further includes a driving member 410 and a retaining member 412. In this embodiment, however, a rod 460 of the retaining member 412 is separate from a control knob 442 for controlling a rotation of the rod 460.

The driving member 410 may be substantially similar to the driving members 110-310 described above, including a housing 436 for housing the control knob 442, a shaft 438 extending distally from the housing 436 to a distal end 414 for engaging a driving recess of the bone screw 404 and a coupling element 440 extending proximally from the housing 436 to engage a corresponding portion of the power driver 408. A channel 444 extends longitudinally through the driving member 410 and is sized and shaped to receive the rod 460 of the retaining member 412 therein. The housing 436 is sized and shaped to receive the control knob 442 therein. The housing 436 may include one or more openings 437 and/or cut outs extending through a wall thereof so that the channel 444 is open to an exterior of the housing 436 via the openings 437. Thus, the control knob 442, which is received within a portion of the channel 444 extending through the housing 436, is accessible to a user via the openings 437.

The control knob 442, in this embodiment, is separate from the retaining member 412 and is sized and shaped to be received within the housing 436 so that the control knob 442 is rotatable within the housing 436, about a longitudinal axis thereof, relative to the driving member 410 via, for example, the openings 437. The control knob 442 includes a longitudinal channel 476 extending therethrough for receiving a portion of the rod 460 therein. Similarly to the control knobs 142-342 described above, the control knob 442 may additionally include grooves 462 and/or other gripping features for facilitating a rotation of the control knob 442 relative to the housing 436. In particular, the user's fingers/thumb may engage the gripping features via the openings 437 of the housing 436 to rotate the control knob 442 relative thereto.

The retaining member 412 includes the rod 460 extending from a proximal end 478 to a distal end 418 configured to engage a retaining recess of the bone screw 404. The rod 460 is sized and shaped to be received within the channel 444 of the driving member 410 and is configured to be inserted longitudinally through the channel 444 via an opening at a proximal 458 thereof. In particular, in an operative configuration, the rod 460 is inserted distally through the coupling element 440, through the channel 476 of the control knob 442 received within the housing 436 and into the channel 444 of the shaft 438 so that the distal end 418 extends distally from the distal end 414 of the driving member 410. The proximal end 478 is sized and shaped to act as a stop so that, when the proximal end 478 abuts the proximal end 458 of the retaining member 412, the retaining member 412 is prevented from moving any further distally relative to the driving member 410. The proximal end 478 may also be sized and shaped to act as a push/pull interface, including features for gripping via a user of the device.

A proximal portion 480 of the rod 460, which is configured to be received within the control knob 442, is keyed to the control knob 442 so that, when the proximal portion 480 is received therein, the retaining member 412 is non-rotatable relative to the control knob 442. Thus, a rotation of the control knob 442 will correspondingly rotate the retaining member 412. In one embodiment, the proximal portion 480 of the rod 460 includes longitudinally extending struts 482 for engaging corresponding longitudinal grooves along an interior surface of the channel 476 of the control knob 442. It will be understood by those of skill in the art, however, that the control knob 442 and the retaining member 412 may be keyed relative to one another in any of a number of ways so long a rotation of the control knob 442 will correspondingly rotate the retaining member 412, in the operative configuration.

Once the driving member 410, the control knob 442 and the retaining member 412 have been assembled to form the driver assembly 406, as described above, the driver assembly 406 is engaged to the bone screw 404 and coupled to the power driver 408 in a manner substantially similar to the system 100. In one embodiment, the proximal end 478 of the retaining member 412 which extends proximally from the proximal end 458 of the driving member 410 is configured to engage a portion of the power driver 408 so that, when engaged therewith, the driving member 410 and the retaining member 412 are rotated as a single unit to maintain a retainment of the bone screw 404 as it is being driven into the bone. In another embodiment, the driver 406 may include a locking mechanism (e.g., a sliding lock) substantially similar to the locking mechanism 154 described above with respect to the system 100. It will be understood by those of skill in the art that the system 400 may be utilized in a manner substantially similar to the system 100 to drive the bone screw 404 into the bone.

As shown in FIGS. 13-18, a driver assembly 506 may be substantially similar to the driving assemblies 106-406, as described above. In particular, the driver assembly 506 is couplable to a power driver to drive a retaining bone screw into a bone and may be utilized with the power driver 108 and the bone screw 104, as described above with respect to the system 100. Similarly to the driver assembly 406, the driver assembly 506 further comprises a driving member 510, a control knob 542 and a retaining member 512. The driving member 510 may be substantially similar to the driving member 410, including a housing 536 housing the control knob 542 therein, a shaft 538 extending distally from the housing 536 to a distal end 514 configured to engage a driving recess of the bone screw, and a coupling element 540 extending proximally from the housing 536 to engage the power driver. The retaining member 512 may be substantially similar to the retaining member 412, including a rod 560 extending from a proximal end 578 to a distal end 518 configured to engage a retaining recess of the bone screw.

Figure 13:
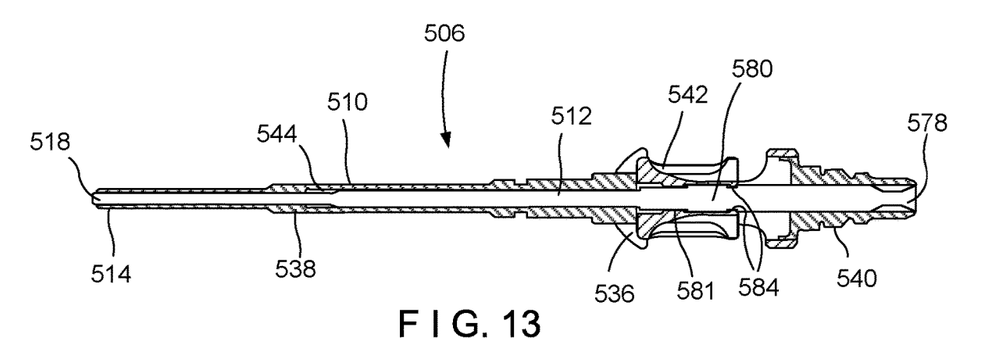
FIG. 13 shows a longitudinal cross-sectional view of a driver assembly according to another exemplary embodiment of the present disclosure.
Figure 14:
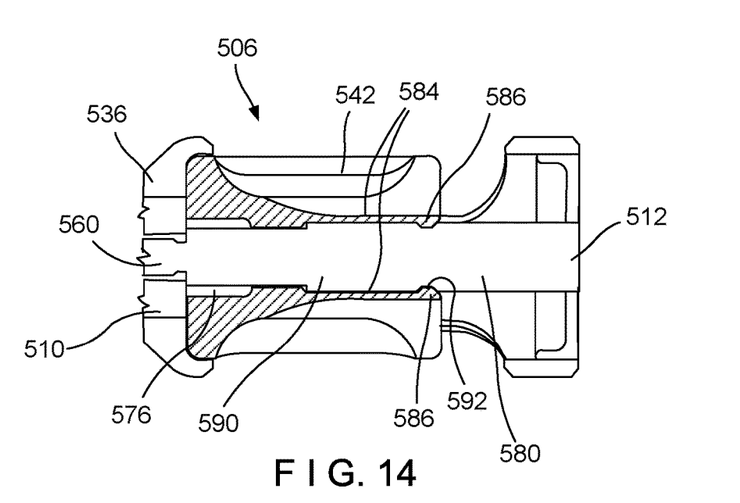
FIG. 14 shows an enlarged cross-sectional view of a portion of the driver assembly according to FIG. 13.

Similarly to the driver assembly 406, the rod 560 is configured to be longitudinally inserted through a channel 544 extending through the driving member 510 so that the rod 560 also passes through a channel 576 of the control knob 542. A proximal portion 580 of the rod 560 to be received within the channel 576 includes a keyed portion 582 so that when received within a corresponding keyed portion 581 of the control knob 542, a rotation of the control knob 542 will correspondingly rotate the retaining member 512. In addition to the keyed portion 582, in this embodiment, the rod 560 and the control knob 542 also engage one another via a spring capture mechanism, which longitudinally fixes the retaining member 512, as will be described in further detail below. Thus, as the control knob 542 is rotated about a longitudinal axis thereof to move the distal end of the retaining member 512 between an engagement with the retaining recess of the bone screw and a disengagement of the retaining recess of the bone screw, the control knob 542 is moved longitudinally within the housing 536.

Figures 15, 16, 17:
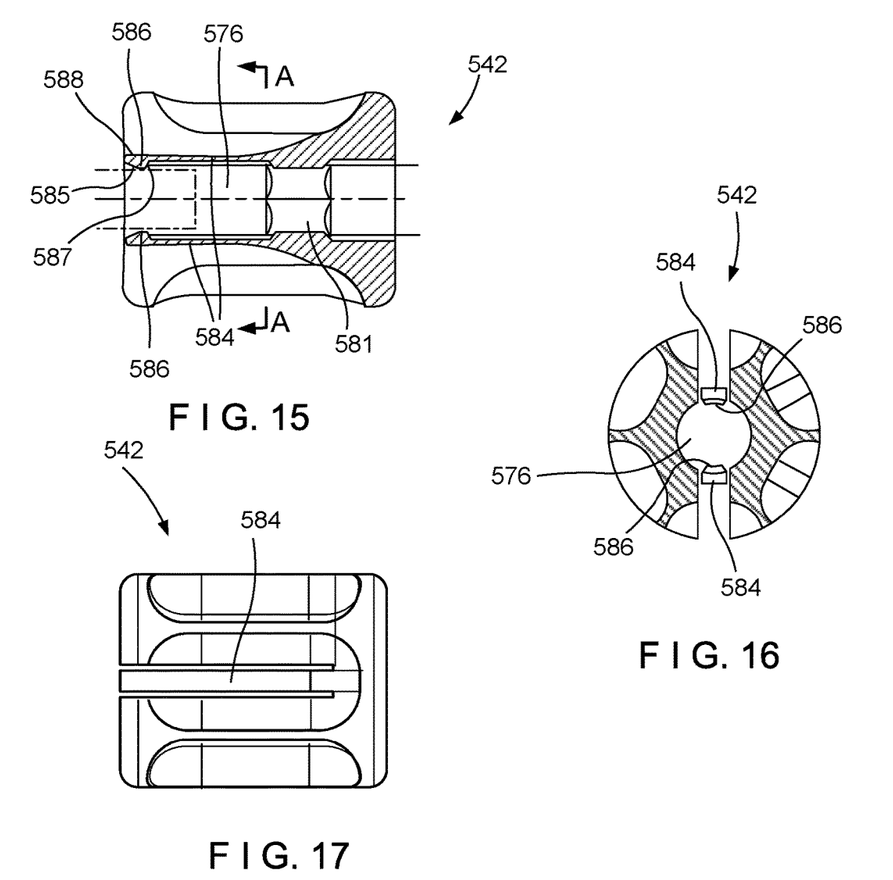
FIG. 15 shows a longitudinal cross-sectional view of a control knob according to the driver assembly according to FIG. 13.
FIG. 16 shows another cross-sectional view of the control knob along a line A-A as shown in FIG. 15.
FIG. 17 shows a side view of the control know according to the driver assembly of FIG. 13.

The control knob 542 is housed within the housing 536 of the driving member 510, as shown in FIGS. 13-14, and includes the channel 576 extending therethrough for receiving the rod 560 of the retaining member 512 therein. As shown in FIGS. 15-17, the control knob 542, in this embodiment, includes the keyed portion 581 along an inner surface of the channel 576 and a pair of spring arms 584 extending proximally therefrom. The keyed portion 581 is sized and shaped to correspond to the keyed portion 582 of the retaining member 512. In one embodiment, the keyed portion 581 may include grooves for receiving correspondingly sized and shaped struts of the retaining member 512, substantially similar to the struts 482 of the retaining member 412. In another embodiment, the keyed portion 581 includes a planar surface for engaging a corresponding planar surface along the proximal portion 580 of the retaining member 512. In one particular embodiment, the keyed portion 581 may have a shaped cross-section such as, for example, a square or hex shape.

The spring arms 584 are biased toward a capture configuration in which a chamfer 586 at a proximal end 588 of each of the spring arms 584 extends into the channel 576 to engage a portion of the retaining member 512 received therein. The chamfer 586, however, is shaped so that, as a distal end of an increased diameter portion 590 of the proximal portion 580 of the rod is pressed distally thereagainst, the spring arms 584 deflect radially outward to permit the distal end of the increased diameter portion 590 to be moved distally past the chamfer 586. In one embodiment, the chamfer 586 includes an angled proximal end 585 for facilitating deflection of the spring arms 584 via sliding of the increased diameter portion 590 therepast. The increased diameter portion 590 is slid distally along the chamfer 586 until the chamfer 586 is received within a correspondingly sized and shaped groove 592 extending about the increased diameter portion 590, which permits the spring arms 584 to revert to their biased configuration, so that the chamfer 586 is locked within the groove 592. In one embodiment, a distal end 587 of the chamfer 586 extends substantially perpendicularly relative to the longitudinal axis to engage a surface of the groove 592 so that, once the chamfer 586 is received within the groove 592, a proximal movement of the retaining rod 512 relative to the driving member 510 does not disengage the retaining member 512 from the control knob 542.

Each of the pair of spring arms 584 may be diametrically opposed relative to one another. In another embodiment, however, the spring arms 584 may extend in any configuration about the channel 576. It will be understood by those of skill in the art, that although the control knob 542 is shown and described as including a pair of spring arms 584, the control knob 542 may include any number of spring arms 584 positioned thereabout in any of a number of configurations so long as the spring arms 584 are configured to longitudinally capture and/or lock the rod 560 of the retaining member 512, as described above.

Figure 18:
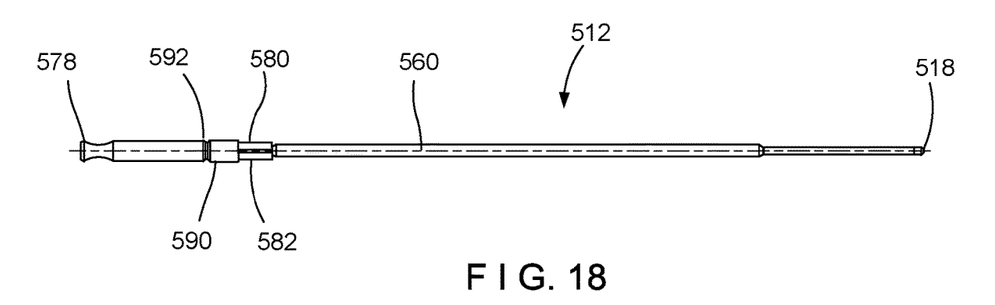
FIG. 18 shows a side view of a retaining member according to the driver assembly according to FIG. 13.

As shown in FIG. 18, the retaining member 512 is substantially similar to the retaining member 412, including the rod 560 extending longitudinally from the proximal end 578 to the distal end 518, which is configured to engage the retaining recess of the bone screw. The rod is sized and shaped to be received within the channel 544 of the driving member 510 and the channel 576 of the control knob 542. In particular, the proximal portion 580 of the rod 560 is configured to be received within and engaged with the channel 576. The keyed portion 582 of the proximal portion 580 is sized and shape to correspond to the size and shape of the keyed portion 581 of the channel 576 of the control knob 542 to prevent a rotation of the retaining member 512 relative to the control knob 542, when the keyed portions 581, 582 of the control knob 542 and the retaining member 512, respectively, engage one another. In one embodiment, the keyed portion 582 may include struts. In another embodiment the keyed portion 582 includes a planar surface. An in yet another embodiment, the keyed portion 582 may be square or hex-shaped.

The increased diameter portion 590 extends proximally of the keyed portion 582 along the proximal portion 580. As described above, the increased diameter portion 590 includes the groove 592 for engaging the chamfer 586 of the spring arms 584 of the control knob 542. In one embodiment, the groove 592 extends about a circumference of the increased diameter portion. The groove 592 is configured to engage the chamfer 586 so that, when engaged, the retaining member 512 is longitudinally locked with respect to the control knob 542. Thus, when the retaining member 512 is inserted through the driving member 510 and engaged with the control knob 542, as described above, the control knob 542 may be rotated about a longitudinal axis thereof to engage/disengage the distal end 518 of the retaining member 512 with the retaining recess of the bone screw 504. As will be understood by those of skill in the art, the control knob 542 is moved longitudinally within the housing 536 as the retaining member 512 is engaged/disengaged with the bone screw 504. The driver assembly 506 may be used to drive the bone screw 504 into a bone, in a manner substantially similar to the systems described above.

Figure 19:
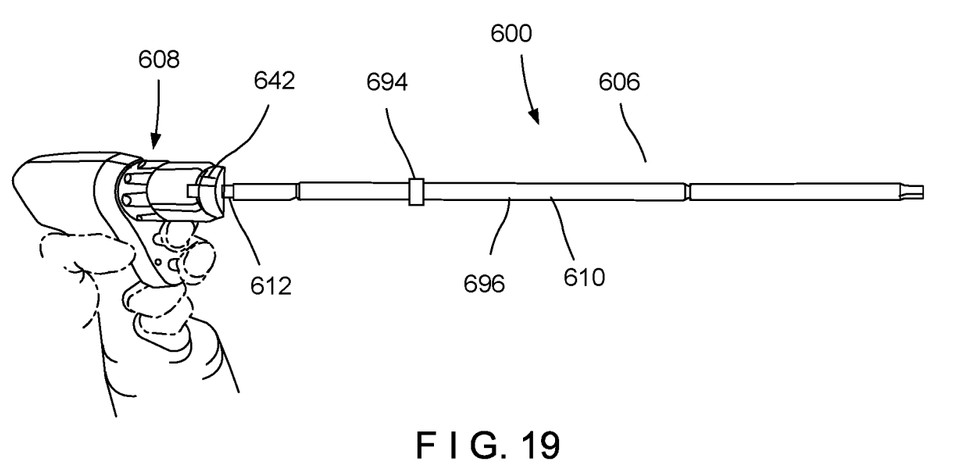
FIG. 19 shows a side view of a system according to another exemplary embodiment of the present disclosure.
Figure 20:
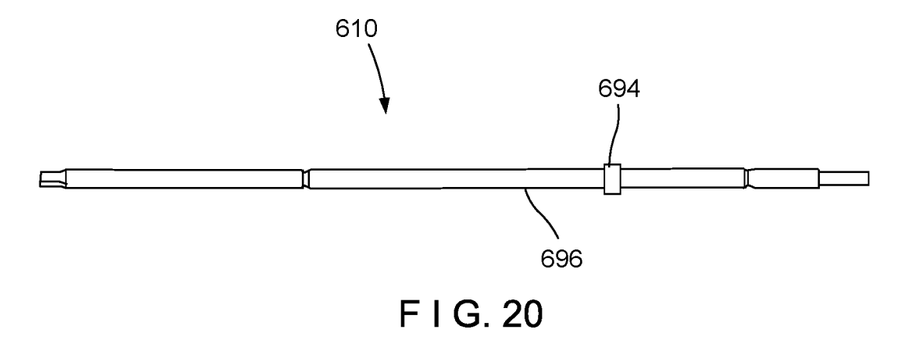
FIG. 20 shows a longitudinal side view of a driving member according to the system of FIG. 19.

As shown in FIGS. 19-20, a system 600 according to another exemplary embodiment of the present disclosure may be substantially similar to the systems described above, the system 600 comprising a driver assembly 606 couplable to a power driver 608 for driving a retaining bone screw into a bone. Similarly to the systems above, the driver assembly 606 includes a driving member 610 for driving the bone screw and a retaining member 612 assembled with the driving member 610 to retain the bone screw while the bone screw is being driven into the bone. A movement of the retaining member 612 relative to the driving member 610 to engage/disengage the retaining member to/from the bone screw is controlled via a control knob 642, which is rotatable about a longitudinal axis thereof, relative to the driving member 610. In this embodiment, however, the driving member 610 includes a stop 694 along a portion thereof for controlling a depth of the bone screw being power-driven into the bone.

It will be understood by those of skill in the art that the driver assembly 606 may be substantially similar to any of the driving assemblies 106-506 described above. The driver assembly 606, however, additionally includes the stop 694 along an exterior surface 696 thereof. The stop 694 is positioned along the exterior surface 696 of the driving member 610 so that when the stop 694 abuts a portion of, for example, an aiming arm and/or a protective sleeve that guides the bone screw to a target area of the bone, the bone screw is inserted into the bone at a desired depth. The driver assembly 606 may then be disengaged and removed from the bone so that a remaining length of the bone screw may be driven into the bone via a manual screwdriver so that a user (e.g., surgeon) finalize insertion of the bone screw based on tactile feel.

The system 600 may be particularly useful for bone screw insertion into a head portion of a bone—e.g., insertion into a femoral head—to alleviate risk of damaging the bone at high speed and/or risk of damage to surrounding tissue resulting from an over-insertion of the bone screw. For example, when preparing the femoral head to receive the bone screw therein, the user may utilize a stepped reamer to drill a channel into the bone for receiving the bone screw. The stepped reamer forms a hole that has a smaller diameter along a distal portion of the channel in the bone than a proximal portion of the channel in the bone. The stop 694 may be positioned along the driving member 610 so that, when the screw is driven into the bone via the power-driven driver assembly 606, the stop 694 abuts the aiming arm when a distal end of the bone screw just reaches the distal portion of the channel in the bone. A remaining length of the bone screw may be driven into the bone via a manual screwdriver.

Although the system 600 has been describe with respect to insertion of the bone screw into a femoral head, it will be understood by those of skill in the art that the system 600 may be utilized for the treatment of any of a number of different bones and/or the insertion of bone screws into any portion of a bone. In another embodiment, the stop 694 may be positioned along the driving member 610 such that the bone screw is fully inserted into the bone, when the stop 694 abuts the aiming arm and/or protective sleeve.

Figure 21:
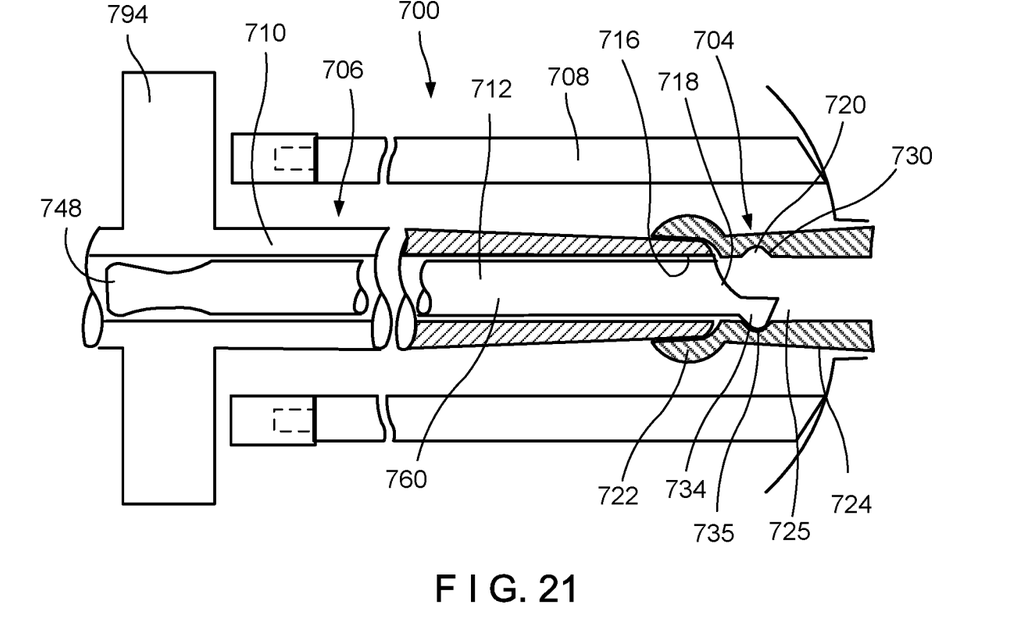
FIG. 21 shows a cross-sectional view of a system according to yet another exemplary embodiment of the present disclosure.

As shown in FIG. 21, a system 700 may be substantially similar to the system 600 described above, comprising a driver assembly 706 configured to power drive a retaining bone screw 704 into a bone. In particular, the driver assembly 706 comprises a driving member 710 configured to engage a driving recess 716 of the bone screw 704 and a retaining member 712 configured to engage a retaining feature 720 of the bone screw 704. Similarly to the driver assembly 606, the driving member 710 of the driver assembly 706 includes a stop 794 configured to abut a portion of an aiming arm and/or protective sleeve 708 being used for the insertion of the bone screw 704, when the bone screw 704 has been inserted to a desired depth within the bone. As described above, the bone screw 704 may be power driven into the bone to a desired depth so that final insertion of the bone may be achieved via a manual screwdriver to alleviate risk of damage to the bone and/or surrounding tissue. In this embodiment, however, the retaining member 712 and the bone screw 704 engage one another via a self-releasing mechanism, as will be described in further detail below.

The bone screw 704 may be substantially similar to the bone screw 104, described above with respect to the system 100, including a head 722 and a body portion 724 extending distally therefrom to threadedly engage the bone. In one embodiment, the bone screw 104 may include a cannulation 725 extending longitudinally therethrough. The head 722 includes a driving recess 716 substantially similar to the driving recess 116. Distally of the driving recess 716, the bone screw 704 includes the retaining feature 720. Rather than a threading, however, the retaining feature 720 may include a circumferential groove 730 extending along an interior surface of the cannulation 725. As will be described in further detail below, the groove 730 is sized and shaped to receive a corresponding portion of the retaining member 712 therein.

The retaining member 712 includes a rod 760 extending longitudinally from a proximal end 748 to a distal end 718 configured to engage the retaining feature 720. The distal end 718, in this embodiment, includes a spring tab 734 extending distally therefrom. The spring tab 734 is biased toward a retaining configuration in which, when the retaining feature 712 is engaged with the bone screw 704, a radially outwardly extending protrusion 735 at of the spring tab 734 extends into the groove 730. In a non-retaining configuration, the spring tab 734 deflects radially inward as the distal end 718 is inserted distally past the driving recess 716 via, for example, a surface of the cannulation 725. Once the protrusion 735 is received within the groove 730, however, the spring tab 734 reverts to its biased, retaining configuration to engage the bone screw 704.

Figure 22:
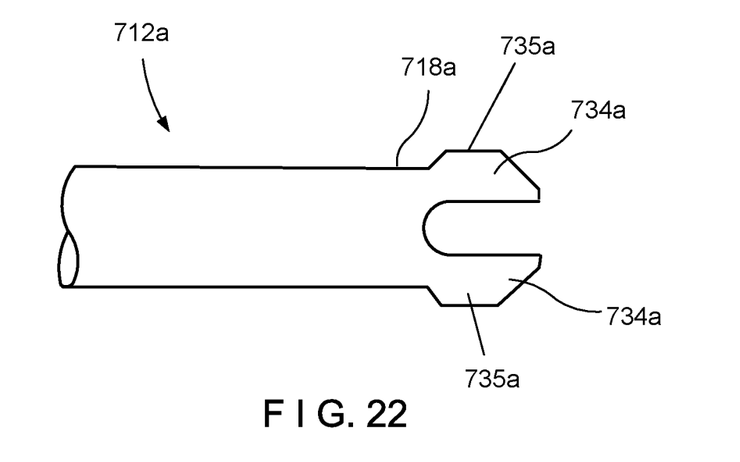
FIG. 22 shows a side view of a distal portion of a retaining member according to an alternate embodiment of the system of FIG. 21.

Although the retaining member 712 is described as including a single spring tab 734, it will be understood by those of skill in the art that the retaining member 712 may include more than one spring tab 734. In an alternate embodiment, as shown in FIG. 22, for example, a distal end 718*a* of a retaining member 712*a* includes two spring tabs 734*a*. Each of the spring tabs 734*a* include a radially outwardly extending protrusion 735*a* configured to be received within a corresponding circumferential groove of a bone screw (e.g., circumferential groove 730 of bone screw 704). In one embodiment, the spring tabs 734*a* may be diametrically opposed from one another. It will be understood by those of skill in the art, however, that the spring tabs 734*a* may be positioned in any of a number of different configurations relative to one another.

The spring tab 734 of the retaining member 712 (and the spring tabs 734*a* of retaining member 712*a*) is configured so that the bone screw 704 is self-released therefrom when the bone screw 704 has been inserted into a desired depth within the bone. In particular, upon engagement with the driver assembly 706, the bone screw 704 is power driven into a target portion of the bone until the stop 794 abuts a portion of an aiming arm and/or protective sleeve 708. A continued torsional force applied to the bone screw 704 via a rotation of the driver assembly 706 even after the stop 794 has contacted the aiming arm and/or protective sleeve 708, however, will cause the bone screw 704 to self-release. The spring tab 734 will deflect radially inward as the bone screw 704 advances distally relative thereto.

In one example, the stop 794 may be configured to drive the bone screw 704 into the bone so that the head portion 722 of the bone screw 704 is 10 mm from a near cortex of the bone. A continued torsional force applied via rotation of the driver assembly 706 by the power driver, however, will cause the bone screw 704 to advance an additional 5 mm so that the bone screw 704 is released from the distal end 718 of the retaining member 712. The bone screw 704 may be manually driven into the bone a remaining distance.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A device for inserting a bone screw into a bone, comprising:
    a driving member including a housing, a shaft extending distally from the housing to a distal end configured to engage a driving recess of a bone screw, and a coupling element extending proximally from the housing to be coupled to a power driver, a channel extending longitudinally through the driving member;
    a control knob configured to be housed within the housing so that a channel of the control knob is in coaxial alignment with the channel of the driving member; and
    a retaining member including a rod extending longitudinally from a proximal end to a distal end configured to be inserted into and to mechanically engage a retaining feature of the driving recess of the bone screw, the rod sized and shaped to be longitudinally inserted through the channels of the driving member and the control knob, a proximal portion of the rod configured to engage the channel of the control knob in an assembled configuration.

2. The device of claim 1, wherein the distal end of the rod includes a threading for threadedly engaging a corresponding threading of the retaining feature of the bone screw.

3. The device of claim 1, wherein the proximal portion of the rod is keyed to a portion of the channel of the control knob so that a rotation of the control knob correspondingly rotates the rod.

4. The device of claim 1, wherein the control knob is longitudinally movable within the housing.

5. The device of claim 1, wherein the distal end of the shaft is configured to engage the driving recess in a head portion of the bone screw and the distal end of the rod is configured to engage the retaining feature in the head portion of the bone screw.

6. The device of claim 5, wherein the retaining feature is formed as a recess extending distally into the bone screw from a distal end of the driving recess.

7. The device of claim 6, wherein a cross-sectional area of the retaining recess is smaller than a cross-sectional area of the driving recess so that the distal end of the shaft is prevented from entering the retaining recess.

8. The device of claim 7, wherein a cross-sectional area of the distal end of the retaining member is selected to be smaller than the cross-sectional area of the retaining recess so that the distal end of the retaining member may be inserted through the driving recess into the retaining recess.

\* \* \* \* \*